United States Patent
Noda et al.

(10) Patent No.: US 9,535,004 B2
(45) Date of Patent: Jan. 3, 2017

(54) SURFACE PLASMON RESONANCE FLUORESCENCE ANALYSIS METHOD AND SURFACE PLASMON RESONANCE FLUORESCENCE ANALYSIS DEVICE

(71) Applicant: KONICA MINOLTA, INC., Chiyoda-ku (JP)

(72) Inventors: Tetsuya Noda, Tokyo (JP); Masataka Matsuo, Tokyo (JP); Yoshimasa Hamano, Tokyo (JP); Hiroshi Hirayama, Tokyo (JP)

(73) Assignee: Konica Minolta, Inc., Tokyo (JP)

( * ) Notice: Subject to any disclaimer, the term of this patent is extended or adjusted under 35 U.S.C. 154(b) by 0 days.

(21) Appl. No.: 15/031,825

(22) PCT Filed: Oct. 30, 2014

(86) PCT No.: PCT/JP2014/078932
§ 371 (c)(1),
(2) Date: Apr. 25, 2016

(87) PCT Pub. No.: WO2015/064704
PCT Pub. Date: May 7, 2015

(65) Prior Publication Data
US 2016/0245746 A1    Aug. 25, 2016

(30) Foreign Application Priority Data

Oct. 31, 2013  (JP) ................. 2013-226667

(51) Int. Cl.
*G01N 21/55* (2014.01)
*G01N 21/13* (2006.01)
*G01N 21/552* (2014.01)
*G01N 21/64* (2006.01)

(52) U.S. Cl.
CPC ............ *G01N 21/553* (2013.01); *G01N 21/13* (2013.01); *G01N 21/648* (2013.01); *G01N 2021/135* (2013.01)

(58) Field of Classification Search
CPC ...... G01N 21/55; G01N 21/553; G01N 21/13; G01N 21/135
USPC ....................................... 356/445
See application file for complete search history.

(56) References Cited

U.S. PATENT DOCUMENTS

2007/0070350 A1    3/2007  Sugiyama et al.
2013/0078146 A1*   3/2013  Sando ................. G01N 21/648
                                                 422/69

FOREIGN PATENT DOCUMENTS

| JP | 2007-93250 | 4/2007 |
| JP | 2009-288103 | 12/2009 |
| WO | WO 2011/152064 | 12/2011 |
| WO | WO 2012/108323 | 8/2012 |

* cited by examiner

*Primary Examiner* — Roy M Punnoose
(74) *Attorney, Agent, or Firm* — Cozen O'Connor

(57) ABSTRACT

In the present invention, excitation light is irradiated onto an analysis chip that has been placed in a chip holder, reflected light or transmitted light from the analysis chip is detected, and as a result the position information of the analysis chip is obtained. On the basis of this position information, the chip holder is moved by a conveyance stage and thereby moved to a measurement position. Excitation light is irradiated onto the analysis chip that is disposed at the measurement position, and fluorescence emitted from a fluorescent substance that marks the substance to be detected is detected.

8 Claims, 11 Drawing Sheets

SURFACE PLASMON RESONANCE FLUORESCENCE ANALYSIS METHOD AND SURFACE PLASMON RESONANCE FLUORESCENCE ANALYSIS DEVICE

RELATED APPLICATIONS

This is a U.S. National Phase Application under 35 USC 371 of International Application PCT/JP2014/078932 filed on Oct. 30, 2014.

This application claims the priority of Japanese application no. 2013-226667 filed Oct. 31, 2013, the entire content of which is hereby incorporated by reference.

TECHNICAL FIELD

The present invention relates to a surface plasmon resonance fluorescence analysis method and a surface plasmon resonance fluorescence analysis device which detect a substance to be detected in a sample solution with use of surface plasmon resonance (SPR).

BACKGROUND ART

When a very small amount of substance can be quantitatively detected with high sensitivity in measurement for detection of biological substances such as protein and DNA, determination of the patient's condition and treatment can be promptly carried out. In view of this, an analysis method and an analysis device for quantitatively detecting weak light generated by a very small amount substance to be detected with high sensitivity are demanded. As an example of a method of detecting a substance to be detected with high sensitivity, a surface plasmon resonance fluorescence analysis method (Surface Plasmon-field enhanced Fluorescence Spectroscopy (SPFS)) is known.

The SPFS uses a prism having a metal film disposed on a predetermined surface. When the metal film is irradiated with excitation light through the prism at an angle which causes surface plasmon resonance, localized light (intensified electric field) can be generated on the surface of the metal film. With the localized light, a fluorescence material labelling the substance to be detected captured on the metal film is excited, and therefore the presence or the amount of the substance to be detected can be detected by detecting the fluorescence emitted from the fluorescence material.

In the SPFS, it is necessary to carry out positioning of the analysis chip with high accuracy in order to achieve detection with high sensitivity and high accuracy. While the incident angle of the excitation light is required to be adjusted with high accuracy to correctly detect the amount (density) of a substance to be detected, the incident angle of the excitation light cannot be adjusted with high accuracy when the position of the analysis chip is shifted. In addition, while it is preferable that the shape and the position of the irradiation spot of the excitation light and the shape and the position of the reaction site on the metal film coincide with each other to detect a substance to be detected with high sensitivity, the shape and the position of the irradiation spot of the excitation light cannot be adjusted with high accuracy when the position of the analysis chip is shifted when the position of the analysis chip is shifted. From the standpoint of usability, it is not preferable to require the user to carry out positioning of the analysis chip with high accuracy.

Some methods, which are not the SPFS, of positioning of an analysis chip have been proposed as the method of detecting a substance to be detected by irradiating an analysis chip with light. For example, PTL 1 discloses a technique in which two position confirmation holes are formed in an analysis chip (flow cell) in detection utilizing an SPR method. The user can adjust the position of the analysis chip with use of the position confirmation holes. In addition, PTL 2 discloses a technique in which an analysis chip (bio-chip) is irradiated with illuminating light having a wavelength different from that of excitation light to detect reflection light or transmission light of the illuminating light and specify the position of the analysis chip in detection utilizing a fluorescence material. With use of the illuminating light having a wavelength different from that of the excitation light, the position of the analysis chip can be specified while preventing discoloration of the fluorescence material.

CITATION LIST

Patent Literatures

PTL 1
Japanese Patent Application Laid-Open No. 2009-288103
PTL 2
Japanese Patent Application Laid-Open No. 2007-093250

SUMMARY OF INVENTION

Technical Problem

The positioning method disclosed in PTL 1 has a problem of increase of manufacturing cost of the analysis chip since two position confirmation holes are required to be formed, and, in addition, a problem of poor usability since the user is required to carry out positioning.

In addition, the positioning method disclosed in PTL 2 has a problem of increase of manufacturing cost of the analysis device since a light source different from that of the excitation light source, a wavelength limitation filter and the like are additionally required.

An object of the present invention is to provide a surface plasmon resonance fluorescence analysis method and a surface plasmon resonance fluorescence analysis device which can carry out positioning of an analysis chip with high accuracy while preventing increase of the manufacturing cost of the analysis chip and the analysis device.

Solution to Problem

To solve the above-mentioned problems, a surface plasmon resonance fluorescence analysis method according to an embodiment of the present invention is a method in which fluorescence which is emitted from a fluorescence material labelling a substance to be detected when the fluorescence material is excited by localized light based on surface plasmon resonance is detected to detect presence or an amount of the substance to be detected, and the surface plasmon resonance fluorescence analysis method includes: installing an analysis chip to a chip holder fixed to a conveyance stage, the analysis chip including a prism having an incidence surface and a film formation surface, a metal film disposed on the film formation surface, and a capturing body fixed on the metal film; obtaining location information of the analysis chip by irradiating the analysis chip installed to the chip holder with excitation light, and by detecting reflection light or transmission light of the excitation light; moving the analysis chip to a measurement position by moving the chip holder by the conveyance stage based on the location information; and irradiating the analysis chip disposed at the measurement position with the excitation light and detecting the fluorescence emitted from the fluorescence material labelling the substance to be detected captured by the capturing body.

In addition, to solve the above-mentioned problems, a surface plasmon resonance fluorescence analysis device according to the embodiment of the present invention is a device in which fluorescence which is emitted from a fluorescence material labelling a substance to be detected when the fluorescence material is excited by localized light based on surface plasmon resonance is detected to detect presence or an amount of the substance to be detected, and the surface plasmon resonance fluorescence analysis device includes: a chip holder configured to detachably hold an analysis chip, the analysis chip including a prism including an incidence surface and a film formation surface, a metal film disposed on the film formation surface, and a capturing body fixed on the metal film; a conveyance stage configured to move the chip holder; an excitation light irradiation section configured to irradiate the analysis chip held by the chip holder with excitation light; an excitation light detection section configured to detect the excitation light reflected by the analysis chip or the excitation light transmitted through the analysis chip; a position adjusting section configured to, based on a detection result of the excitation light detection section, specify a position of the analysis chip held by the chip holder, and move the chip holder by the conveyance stage to move the analysis chip to a measurement position; and a fluorescence detection section configured to detect the fluorescence emitted from the fluorescence material labelling the substance to be detected captured by the capturing body.

Advantageous Effects of Invention

According to the present invention, highly accurate positioning of an analysis chip can be carried out without disturbing the user only by additionally providing an inexpensive light receiving sensor. Therefore, according to the present invention, it is possible to achieve detection of a substance to be detected with high sensitivity and high accuracy while preventing increase of the manufacturing cost and reduction in usability.

DESCRIPTION OF EMBODIMENT

In the following, an embodiment of the present invention is described in detail with reference to the accompanying drawings.

Figure 1:
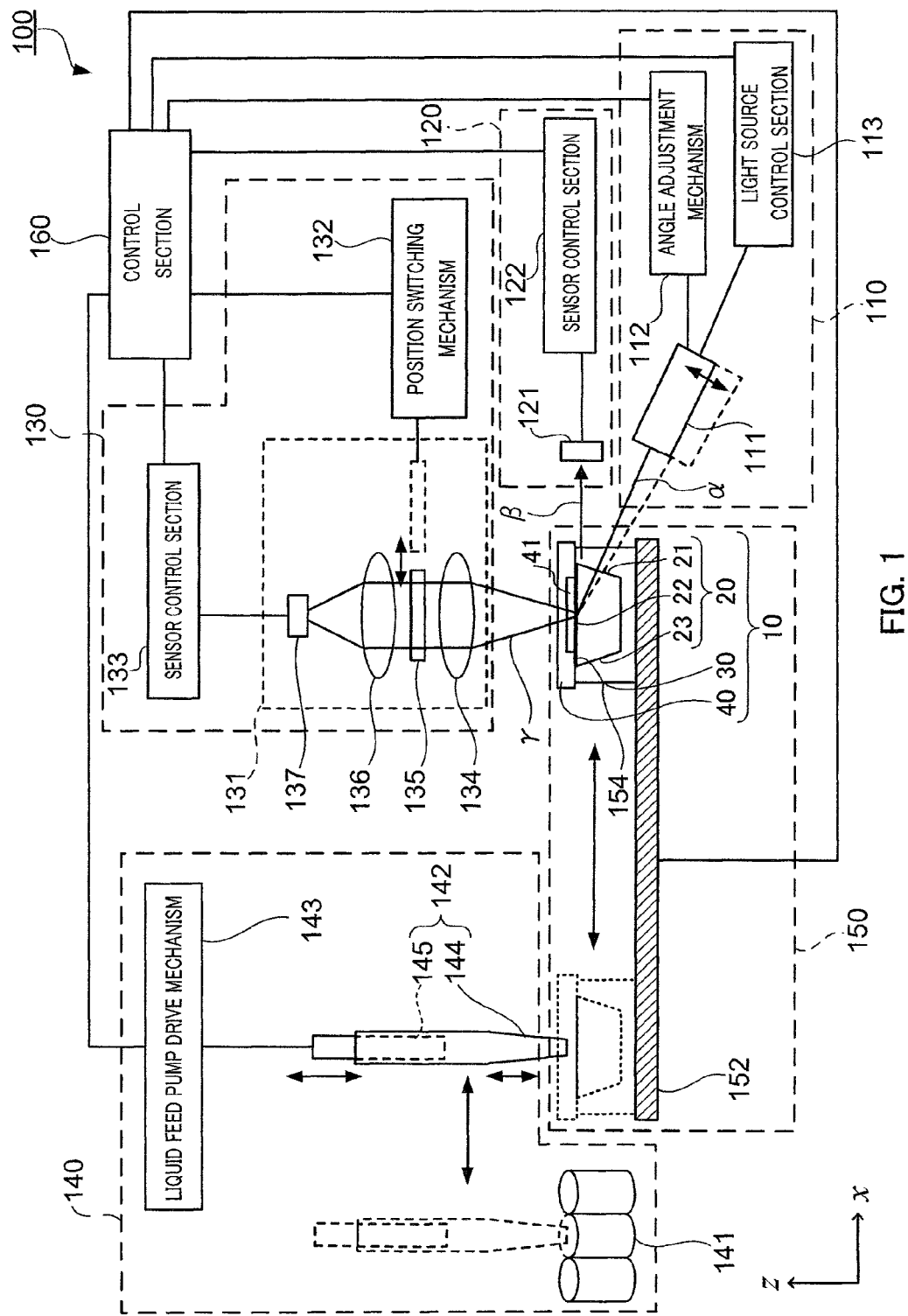
FIG. 1 schematically illustrates a configuration of an SPFS device according to an embodiment of the present invention.

FIG. 1 is a schematic view illustrating a configuration of surface plasmon resonance fluorescence analysis device (SPFS device) 100 according to an embodiment of the present invention. As illustrated in FIG. 1, SPFS device 100 includes excitation light irradiation unit 110, excitation light detection unit 120, fluorescence detection unit 130, liquid feed unit 140, conveyance unit 150 and control section 160. SPFS device 100 is used in a state where analysis chip 10 is attached to chip holder 154 of conveyance unit 150. For such a configuration, analysis chip 10 is described first, and each component of SPFS device 100 is described after the description of analysis chip 10.

Analysis chip 10 includes prism 20 having incidence surface 21, film formation surface 22 and emission surface 23, metal film 30 formed on film formation surface 22, and channel closure 40 disposed on film formation surface 22 or metal film 30. Normally, analysis chip 10 is replaced for each analysis. Analysis chip 10 is preferably a structure with each side of several millimeters to several centimeters, but may be a smaller or larger structure which is not categorized as "chip."

Prism 20 is a dielectric which is transparent to excitation light α. Prism 20 includes incidence surface 21, film formation surface 22 and emission surface 23. Incidence surface 21 is a surface through which excitation light α from excitation light irradiation unit 110 enters prism 20. Metal film 30 is disposed on film formation surface 22. Excitation light α having entered prism 20 is reflected by the rear surface of metal film 30. To be more specific, excitation light α is reflected by an interface (film formation surface 22) between prism 20 and metal film 30. Emission surface 23 is a surface through which excitation light α reflected by metal film 30 is emitted out of prism 20.

The shape of prism 20 is not limited. In the present embodiment, the shape of prism 20 is a column whose bottom surface is a trapezoid. The surface corresponding to a bottom side of the trapezoid is film formation surface 22. The surface corresponding to one of the legs is incidence surface 21, and the surface corresponding to the other of the legs is emission surface 23. Preferably, the trapezoid serving as the bottom surface is an isosceles trapezoid. With such a configuration, incidence surface 21 and emission surface 23 are symmetrical, and the S wave component of excitation light α does not easily remain in prism 20.

Incidence surface 21 is formed such that excitation light α does not return to excitation light irradiation unit 110. When excitation light α returns to a laser diode (hereinafter also referred to as "LD") in the case where the light source of excitation light α is the LD, the excitation state of the LD is disturbed, and the wavelength and the output of excitation light α are varied. In view of this, the angle of incidence surface 21 is set within a scanning range around the ideal enhanced angle such that that excitation light α is not perpendicularly incident on incidence surface 21. In the present embodiment, each of the angle between incidence surface 21 and film formation surface 22 and the angle between film formation surface 22 and emission surface 23 is approximately 80 degrees.

It is to be noted that the resonance angle (and the enhanced angle in the close vicinity of the resonance angle) largely depends on the design of analysis chip 10. The design factors are the refractive index of prism 20, the refractive index of metal film 30, the film thickness of metal film 30, the extinction coefficient of metal film 30, the wavelength of excitation light $\alpha$, and the like. While the resonance angle and the enhanced angle are shifted by a substance to be detected fixed on metal film 30, the shift amount is smaller than several degrees.

Prism 20 has a birefringence property to a certain degree. Examples of the material of prism 20 include a resin and glass. Preferably, the material of prism 20 is a resin which has a refractive index of 1.4 to 1.6 and causes a small birefringence.

Metal film 30 is disposed on film formation surface 22 of prism 20. Thus, interaction (surface plasmon resonance) is caused between the photon of excitation light $\alpha$ which is incident on film formation surface 22 under the total reflection condition and the free electron in metal film 30, and thus localized-field light can be generated on the surface of metal film 30.

The material of metal film 30 is not limited as long as surface plasmon resonance can be caused. Examples of the material of metal film 30 include gold, silver, copper, aluminum, and their alloys. In the present embodiment, metal film 30 is a thin film formed of gold. The formation method for metal film 30 is not limited. Examples of the formation method for metal film 30 include sputtering, deposition, and plating. Preferably, the thickness of metal film 30 is, but not limited to, 30 to 70 nm.

In addition, although not illustrated in FIG. 1, a capturing body for capturing the substance to be detected is fixed on the surface (front surface of metal film 30) of metal film 30 on the side opposite to prism 20. When a capturing body is fixed, the substance to be detected can be selectively detected. In the present embodiment, a capturing body is uniformly fixed in a predetermined region (reaction site) on metal film 30. The type of the capturing body is not limited as long as the substance to be detected can be captured. In the present embodiment, the capturing body is an antibody specific to the substance to be detected or a fragment of the antibody.

The channel closure 40 is disposed on metal film 30. When metal film 30 is partly formed on film formation surface 22 of prism 20, channel closure 40 may be disposed on film formation surface 22. A channel groove is formed on the rear surface of channel closure 40, and channel closure 40 forms liquid flow channel 41 together with metal film 30 (and prism 20). Examples of the liquid include sample solution including a substance to be detected, labeling solution including an antibody labeled by a fluorescence material, washing solution and the like. The capturing body fixed on metal film 30 is exposed to the interior of channel 41. Both ends of channel 41 are respectively connected to the inlet and the outlet which are not illustrated and formed on the top surface of channel closure 40. When liquid is injected into channel 41, the liquid makes contact with the capturing body.

Preferably, channel closure 40 is formed of a material which is transparent to fluorescence $\gamma$ emitted from metal film 30. Examples of the material of channel closure 40 include a resin. As long as the part for taking out fluorescence $\gamma$ is transparent to fluorescence $\gamma$, other parts of channel closure 40 may be formed of an opaque material. Channel closure 40 is joined to metal film 30 or prism 20 by bonding using a double-sided tape, adhesive agent and the like, laser welding, ultrasound welding, pressure bonding using a clamp member and the like, for example.

As illustrated in FIG. 1, excitation light $\alpha$ enters prism 20 from incidence surface 21. At this time, part of excitation light $\alpha$ is reflected by incidence surface 21 and becomes reflection light $\beta$. Excitation light $\alpha$ having entered prism 20 is incident on metal film 30 at a total reflection angle (an angle at which surface plasmon resonance is caused). Metal film 30 is irradiated with excitation light $\alpha$ at an angle which causes surface plasmon resonance in the above-mentioned manner, and thus it is possible to generate localized light (which is also generally called "evanescent light" or "near-field light") on metal film 30. With the localized light, the fluorescence material labelling the substance to be detected placed on metal film 30 is excited, and fluorescence $\gamma$ is emitted. By detecting the light amount of fluorescence $\gamma$ emitted from the fluorescence material light, SPFS device 100 detects the presence or the amount of the substance to be detected.

Next, the components of SPFS device 100 are described. As described above, SPFS device 100 includes excitation light irradiation unit 110, excitation light detection unit 120, fluorescence detection unit 130, liquid feed unit 140, conveyance unit 150 and control section 160.

Excitation light irradiation unit 110 emits excitation light $\alpha$ to analysis chip 10 held by chip holder 154. At the time of measurement of fluorescence $\gamma$, excitation light irradiation unit 110 emits only P wave with respect to metal film 30 toward incidence surface 21 such that the incident angle to metal film 30 is an angle at which surface plasmon resonance is caused. Here, "excitation light" is light which directly or indirectly excites a fluorescence material. For example, excitation light $\alpha$ is light which generates localized light which excites a fluorescence material on the surface of metal film 30 when it is emitted to metal film 30 through prism 20 at an angle which causes surface plasmon resonance. In SPFS device 100 according to the present embodiment, excitation light $\alpha$ is used also for positioning of analysis chip 10.

Excitation light irradiation unit 110 includes a configuration for emitting excitation light $\alpha$ toward prism 20, and a configuration for scanning the incident angle of excitation light $\alpha$ to the rear surface of metal film 30. In the present embodiment, excitation light irradiation unit 110 includes light source unit 111, angle adjustment mechanism 112 and light source control section 113.

Light source unit 111 emits collimated excitation light $\alpha$ having a constant wavelength and a constant light amount such that the irradiation spot on the rear surface of metal film 30 has a substantially circular shape. Light source unit 111 includes, for example, a light source of excitation light $\alpha$, a beam shaping optical system, an APC mechanism and a temperature adjustment mechanism (which are not illustrated).

The type of the light source is not limited, and is a laser diode (LD), for example. Other examples of the light source include a light-emitting diode, a mercury lamp, and other laser light sources. In the case where the light emitted from the light source is not a beam, the light emitted from the light source is converted to a beam by a lens, a mirror, a slit or the like. In addition, in the case where the light emitted from the light source is not monochromatic light, the light emitted from the light source is converted to monochromatic light by a diffraction grid or the like. Further, in the case where the light emitted from the light source is not linear polarization, the light emitted from the light source is converted to light of linear polarization by a polarizer or the like.

The beam shaping optical system includes a collimator, a band pass filter, a linear polarization filter, a half-wave plate, a slit, a zooming unit and the like, for example. The beam shaping optical system may include one or more of the above-mentioned components. The collimator collimates excitation light α emitted from the light source. The band pass filter changes excitation light α emitted from the light source to narrowband light composed only of a central wavelength. The reason for this is that excitation light α from the light source has a slight wavelength distribution width. The linear polarization filter changes excitation light α emitted from the light source to linearly polarized light. The half-wave plate adjusts the polarization direction of excitation light α such that the P wave component is incident on metal film 30. The slit and the zooming unit adjust the beam diameter, the outline shape and the like of excitation light α such that the shape of the irradiation spot on the rear surface of metal film 30 has a circular shape having a predetermined size.

The APC mechanism controls the light source such that the output of the light source is maintained at a constant value. To be more specific, the APC mechanism detects the light amount of the light diverged from excitation light α by a photodiode not illustrated and the like. Then, the APC mechanism controls the input energy by a recurrent circuit to control the output of the light source at a constant value.

The temperature adjustment mechanism is composed of a heater, a Peltier device, or the like, for example. The wavelength and the energy of the light emitted from the light source can be varied by the temperature. Therefore, the temperature of the light source is maintained at a constant value by the temperature adjustment mechanism to control the wavelength and the energy of the light emitted from the light source at a constant value.

Angle adjustment mechanism 112 adjusts the incident angle of excitation light α to metal film 30 (the interface between prism 20 and metal film 30 (film formation surface 22)). Angle adjustment mechanism 112 relatively rotates the optical axis of excitation light α and chip holder 154 to emit excitation light α at a predetermined incident angle toward a predetermined position of metal film 30 through prism 20.

For example, angle adjustment mechanism 112 turns light source unit 111 around an axis orthogonal to the optical axis of excitation light α (an axis in a perpendicular direction as seen in FIG. 1). At this time, the position of the rotation axis is set such that the position of the irradiation spot on metal film 30 is not substantially moved when the incident angle is scanned. By setting the position of the rotation center at a position near the intersection of the optical axes of two rays of excitation light α at both ends of the scanning range of the incident angle (at a position between the irradiation position on film formation surface 22 and incidence surface 21), the shift of the irradiation position can be minimized.

In the incident angle of excitation light α to metal film 30, the angle at which the maximum light amount of the plasmon scattering light is obtained is the enhanced angle. By setting the incident angle of excitation light α to the enhanced angle or an angle approximately equal to the enhanced angle, fluorescence γ having a high intensity can be measured. While the basic incident condition of excitation light α is determined by the material and the shape of prism 20 of analysis chip 10, the film thickness of metal film 30, the refractive index of the liquid in the channel and the like, the optimum incident condition is slightly varied depending on the type and the amount of the fluorescence material in the channel, shaping errors of prism 20 and the like. Therefore, it is preferable to determine an optimum enhanced angle at each measurement. In the present embodiment, the preferable emission angle of excitation light α to the normal of metal film 30 (straight line along the z-axis direction in FIG. 1) is approximately 70 degrees.

Light source control section 113 controls components included in light source unit 111 to control emission of emission light (excitation light α) of light source unit 111. Light source control section 113 is composed of a publicly known computer, microcomputer, or the like including a computation device, a control device, a storage device, and an inputting device, for example.

Excitation light detection unit 120 detects reflection light β or transmission light β generated by irradiation of analysis chip 10 with excitation light α for the purpose of positioning of analysis chip 10 at the time of optical measurement (for example, detection of the enhanced angle, measurement of the optical blank value, detection of fluorescence γ and the like). Preferably, excitation light detection unit 120 detects reflection light β or transmission light β' for positioning of analysis chip 10 before performing the first optical measurement. In many cases, the first optical measurement is detection of the enhanced angle, and therefore it is preferable to detect reflection light β or transmission light β' before detection of the enhanced angle. In the case where the detection of the enhanced angle is not performed, reflection light β or transmission light β' is detected before the measurement of the optical blank. In the case where both the detection of the enhanced angle and the measurement of the optical blank are not performed, reflection light β or transmission light β' is detected before detection of fluorescence γ. In the present embodiment, excitation light detection unit 120 detects reflection light β of excitation light α. Excitation light detection unit 120 includes light receiving sensor 121 and sensor control section 122.

Light receiving sensor 121 detects reflection light β of excitation light α. The type of light receiving sensor 121 is not limited as long as reflection light or transmission light of excitation light α can be detected. For example, light receiving sensor 121 is a photodiode (PD). Preferably, the size of the light reception surface of light receiving sensor 121 is greater than the beam diameter of excitation light α. For example, in the case where the beam diameter of excitation light α is about 1 mm to 1.5 mm, the length of each side of the light reception surface of light receiving sensor 121 is preferably 3 mm or greater.

Light receiving sensor 121 is disposed at a position where reflection light β of excitation light α is incident. In the present embodiment, light receiving sensor 121 is disposed at a position where reflection light β from incidence surface 21 is incident. Preferably, light receiving sensor 121 is disposed at a position where reflection light β of excitation light α emitted at an angle for the detection of fluorescence γ or an angle approximately equal to the angle for the detection of fluorescence γ is incident. The irradiation position of excitation light α is slightly varied depending on variation of the incident angle, and therefore, when the incident angle of excitation light α for positioning of analysis chip 10 and the incident angle of excitation light α for measurement of fluorescence γ are equal to or approximately equal to each other, the accuracy of positioning at the time of detection of fluorescence γ can be enhanced. In the present embodiment, in the case where the emission angle of excitation light α to the normal of metal film 30 (straight line along the z-axis direction in FIG. 1) is approximately 70 degrees, reflection light β from incidence surface 21 substantially horizontally advances in the travelling direction of the conveyance stage (x-axis direction in FIG. 1). Accordingly, light receiving sensor 121 is disposed at a position where reflection light β travelling in a horizontal direction is incident (see FIG. 4C).

Sensor control section 122 controls detection of the output value of light receiving sensor 121, management of the sensitivity of light receiving sensor 121 according to the detected output value, change of the sensitivity of light receiving sensor 121 for obtaining an appropriate output value, and the like. Sensor control section 122 is composed of a publicly known computer, microcomputer, or the like including a computation device, a control device, a storage device, and an inputting device, for example.

Fluorescence detection unit 130 detects fluorescence γ generated by irradiation of metal film 30 with excitation light α. In addition, as necessary, fluorescence detection unit 130 also detects plasmon scattering light generated by irradiation of metal film 30 with excitation light α. Fluorescence detection unit 130 includes light reception unit 131, position switching mechanism 132 and sensor control section 133.

Light reception unit 131 is disposed in the normal direction of metal film 30 of analysis chip 10 (the z-axis direction in FIG. 1). Light reception unit 131 includes first lens 134, optical filter 135, second lens 136 and light receiving sensor 137.

First lens 134 is, for example, a condenser lens, and condenses the light emitted from metal film 30. Second lens 136 is, for example, an image forming lens, and images the light condensed by first lens 134 on the light reception surface of light receiving sensor 137. The light paths between the lenses are substantially parallel to each other. Optical filter 135 is disposed between the lenses.

Optical filter 135 guides only the fluorescence component to light receiving sensor 137, and removes the excitation light component (plasmon scattering light) in order to detect fluorescence γ with a high S/N ratio. Examples of optical filter 135 include an excitation light reflection filter, a short wavelength cut filter and a band pass filter. Optical filter 135 is, for example, a filter including a multi-layer film that reflects a predetermined light component, but may be a color glass filter that absorbs a predetermined light component.

Light receiving sensor 137 detects fluorescence γ. Light receiving sensor 137 has a high sensitivity such that weak fluorescence γ from a very small amount of substance to be detected can be detected. Light receiving sensor 137 is, for example, a photomultiplier tube (PMT), an avalanche photodiode (APD) or the like.

Position switching mechanism 132 switches the position of optical filter 135 between a position on the light path and a position outside the light path in light reception unit 131. To be more specific, optical filter 135 is disposed on the light path of light reception unit 131 when light receiving sensor 137 detects fluorescence γ, and optical filter 135 is disposed at a position outside the light path of light reception unit 131 when light receiving sensor 137 detects plasmon scattering light. Position switching mechanism 132 is composed of a rotation driving section, and a publicly known mechanism (such as a turntable and a rack-and-pinion) that moves optical filter 135 in a horizontal direction by utilizing rotational movement, for example.

Sensor control section 133 controls detection of the output value of light receiving sensor 137, management of the sensitivity of light receiving sensor 137 according to the detected output value, change of the sensitivity of light receiving sensor 137 for obtaining an appropriate output value and the like. Sensor control section 133 is composed of a publicly known computer, microcomputer, or the like including a computation device, a control device, a storage device, and an inputting device, for example.

Liquid feed unit 140 supplies sample solution, labeling solution, washing solution and the like into channel 41 of analysis chip 10 held by chip holder 154. Liquid feed unit 140 includes chemical liquid chip 141, syringe pump 142 and liquid feed pump drive mechanism 143.

Chemical liquid chip 141 is a container for housing liquid such as sample solution, labeling solution, and washing solution. Normally, as chemical liquid chip 141, a plurality of containers corresponding to the types of the liquid are disposed, or a chip composed of a plurality of integrated containers is disposed.

Syringe pump 142 is composed of syringe 144, and plunger 145 which can reciprocate in syringe 144. Through reciprocation of plunger 145, suction and ejection of the liquid is quantitatively performed. When syringe 144 is replaceable, washing of syringe 144 is unnecessary. Such a configuration is preferable from the viewpoint of preventing entrance of impurities. When syringe 144 is not replaceable, it is possible to use syringe 144 without replacing syringe 144 by additionally providing a configuration for washing the interior of syringe 144.

Liquid feed pump drive mechanism 143 includes a driving device of plunger 145, and a moving device of syringe pump 142. The driving device of syringe pump 142 is a device for reciprocating plunger 145, and includes a stepping motor, for example. The driving device including a stepping motor can manage the liquid feed amount of syringe pump 142 and the liquid feed speed, and is therefore preferable from the viewpoint of managing the amount of the residual liquid of analysis chip 10. The moving device of syringe pump 142 freely moves syringe pump 142 in the axial direction (for example, a vertical direction) of syringe 144 and a direction (for example, a horizontal direction) crossing the axial direction, for example. The moving device of syringe pump 142 is composed of a robot arm, a biaxial stage or a vertically movable turntable, for example.

Preferably, liquid feed unit 140 further includes a device that detects the position of an end of syringe 144 from the viewpoint of adjusting the relative height of syringe 144 and analysis chip 10 to a constant value, and managing the amount of the residual liquid in analysis chip 10 at a constant value.

Liquid feed unit 140 sucks various kinds of liquid from chemical liquid chip 141, and supplies the liquid into channel 41 of analysis chip 10. At this time, when plunger 145 is moved, the liquid reciprocates in channel 41 in analysis chip 10, and the liquid in channel 41 is agitated. In this manner, uniformization of the density of the liquid, facilitation of reaction (for example, antigen-antibody reaction) in channel 41 can be achieved. From the view point of performing the above-mentioned operations, it is preferable that analysis chip 10 and syringe 144 be configured such that the inlet of analysis chip 10 is protected with a multi-layer film and that the inlet can be sealed when syringe 144 penetrates the multi-layer film.

The liquid in channel 41 is again sucked by syringe pump 142, and ejected to chemical liquid chip 141 and the like. By repeating the above-mentioned operations, reaction, washing and the like of various kinds of liquid can be performed, and a substance to be detected labeled by a fluorescence material can be placed at a reaction site in channel 41.

Conveyance unit 150 conveys analysis chip 10 to a measurement position or a liquid feeding position, and fixes analysis chip 10. Here, the "measurement position" is a position where excitation light irradiation unit 110 irradiates analysis chip 10 with excitation light α, and fluorescence detection unit 130 detects fluorescence γ generated by the irradiation. In addition, the "liquid feeding position" is a position where liquid feed unit 140 supplies liquid into channel 41 of analysis chip 10, or removes the liquid in channel 41 of analysis chip 10. Conveyance unit 150 includes conveyance stage 152 and chip holder 154. Chip holder 154 is fixed to conveyance stage 152 so as to detachably hold analysis chip 10. Chip holder 154 has a shape which can hold analysis chip 10 and does not block the light paths of excitation light α, reflection light β and fluorescence γ. For example, chip holder 154 is provided with opening through which excitation light α, reflection light β and fluorescence γ pass. Conveyance stage 152 moves chip holder 154 in a specific direction (x-axis direction in FIG. 1) and a direction opposite to the specific direction. Conveyance stage 152 is driven by a stepping motor and the like, for example.

Control section 160 controls angle adjustment mechanism 112, light source control section 113, position switching mechanism 132, sensor control section 133, liquid feed pump drive mechanism 143 and conveyance stage 152. In addition, control section 160 functions also as a position adjusting section that, on the basis of a detection result of excitation light detection unit 120, specifies the position of analysis chip 10 held by chip holder 154, and moves chip holder 154 by conveyance stage 152 to move analysis chip 10 to an appropriate measurement position. Control section 160 is composed of a publicly known computer, microcomputer, or the like including a computation device, a control device, a storage device, and an inputting device, for example.

Figure 2:
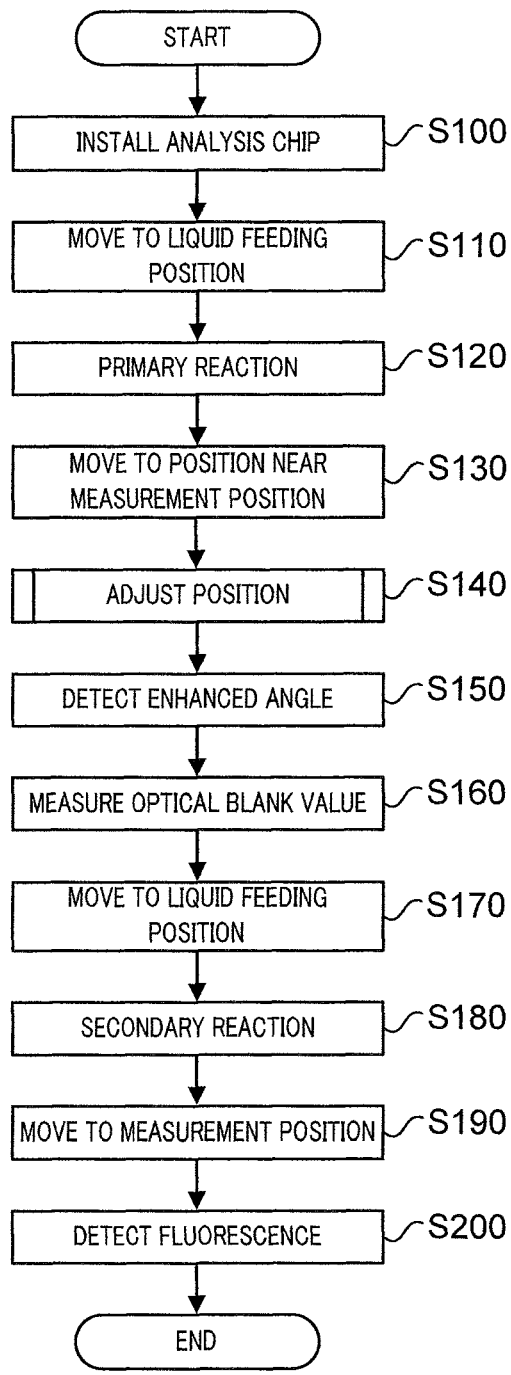
FIG. 2 is a flowchart of an exemplary operation procedure of the SPFS device illustrated in FIG. 1.
Figure 3:
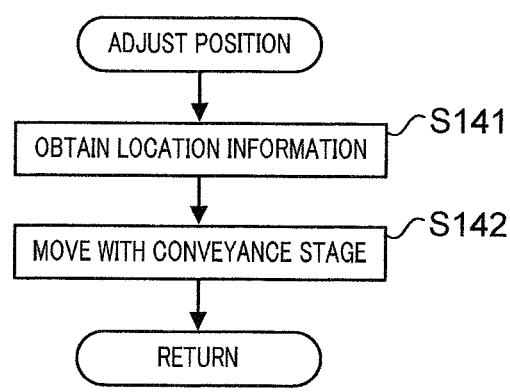
FIG. 3 is a flowchart of a step in a position adjustment step (S140) illustrated in FIG. 2.

Next, a detection operation of SPFS device 100 (the surface plasmon resonance fluorescence analysis method according to the embodiment of the present invention) will be described. FIG. 2 is a flowchart of an exemplary operation procedure of SPFS device 100. FIG. 3 is a flowchart of steps in a position adjustment step (S140) of FIG. 2.

First, analysis chip 10 is installed in chip holder 154 of SPFS device 100 (step S100).

Next, control section 160 operates conveyance stage 152 to move analysis chip 10 to a liquid feeding position (step S110).

Next, control section 160 operates liquid feed unit 140 to introduce the sample solution in chemical liquid chip 141 into channel 41 of analysis chip 10 (step S120). In channel 41, a substance to be detected is captured on metal film 30 by an antigen-antibody reaction (primary reaction). Thereafter, the sample solution in channel 41 is removed, and the interior of channel 41 is washed with the washing solution. It is to be noted that when moisturizing agent is present in channel 41 of analysis chip 10, the interior of channel 41 is washed prior to the introduction of the sample solution to remove the moisturizing agent so that the capturing body can appropriately capture the substance to be detected.

Next, control section 160 operates conveyance stage 152 to move analysis chip 10 to a position near the measurement position (step S130).

Next, control section 160 operates excitation light irradiation unit 110, excitation light detection unit 120 and conveyance stage 152 to obtain the location information of analysis chip 10, and adjusts the position of analysis chip 10 on the basis of the obtained location information (step S140). As illustrated in FIG. 3, at this step, first, analysis chip 10 held by chip holder 154 is irradiated with excitation light α, and reflection light β of excitation light α is detected to obtain the location information of analysis chip 10 (step S141). In this manner, the degree of positional displacement of analysis chip 10 from the measurement position can be specified. Next, on the basis of the obtained location information, chip holder 154 is moved by conveyance stage 152, and analysis chip 10 is disposed at an appropriate measurement position (step S142).

Figure 4A:
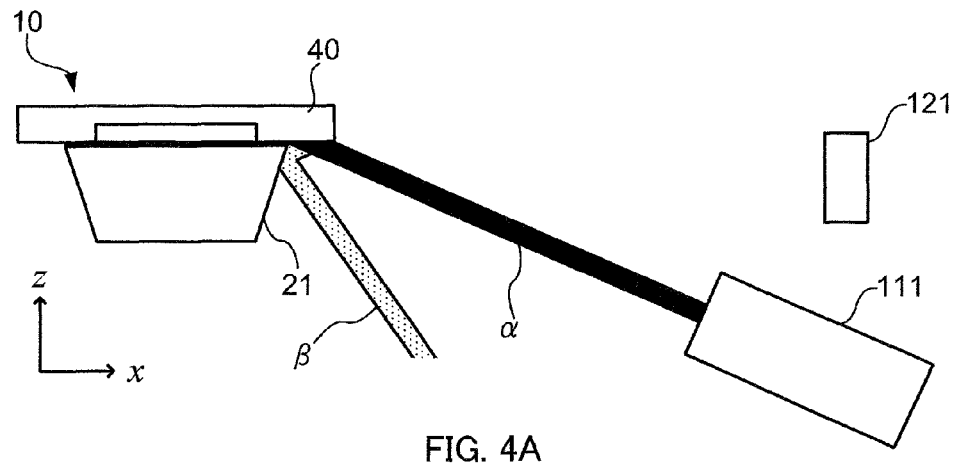
FIGS. 4A to 4C are schematic views for describing a step (S141) of obtaining location information of an analysis chip.
Figure 4B:
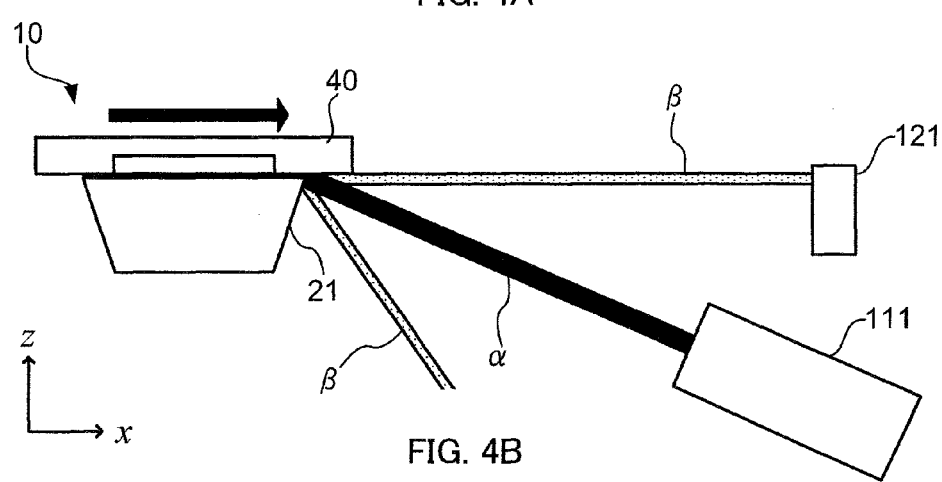
Figure 4C:
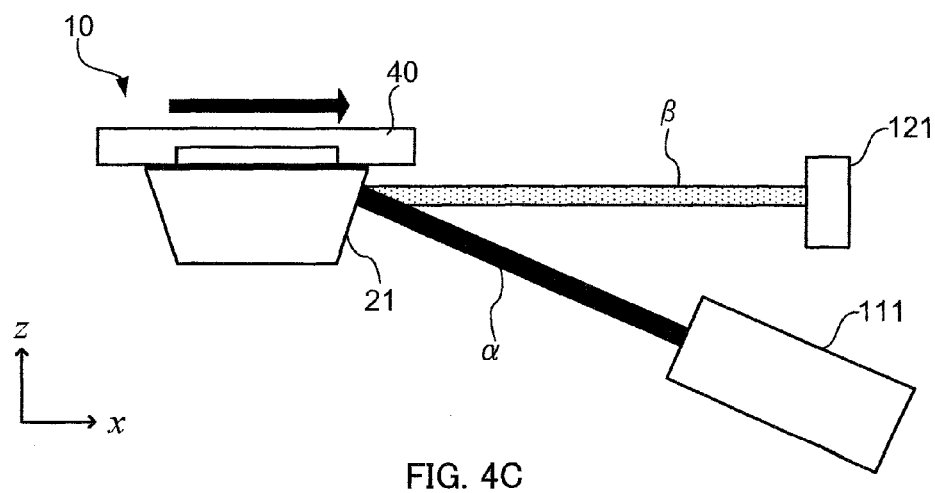

FIGS. 4A to 4C are schematic views for describing a step of obtaining the location information of analysis chip 10 (S141). First, as illustrated in FIG. 4A, when light source unit 111 emits excitation light α in the case where analysis chip 10 is located at a position separated from light source unit 111, excitation light α is reflected by channel closure 40 and travels toward the lower side (conveyance stage 152 side). Thus, reflection light β from analysis chip 10 is not incident on light receiving sensor 121 of excitation light detection unit 120.

In this state, when analysis chip 10 is brought close to light source unit 111, excitation light α from light source unit 111 reaches a boundary (hereinafter referred to as "edge") between prism 20 and channel closure 40. In this case, as illustrated in FIG. 4B, while excitation light α (reflection light β) reflected by channel closure 40 is not incident on light receiving sensor 121, excitation light α (reflection light β) reflected by incidence surface 21 is incident on light receiving sensor 121. Thus, part of reflection light β from analysis chip 10 is incident on light receiving sensor 121.

When analysis chip 10 is further brought close to light source unit 111, the entirety of excitation light α from light source unit 111 reaches incidence surface 21 of prism 20. Thus, as illustrated in FIG. 4C, the entirety of reflection light β from analysis chip 10 is incident on light receiving sensor 121.

Figure 5A:
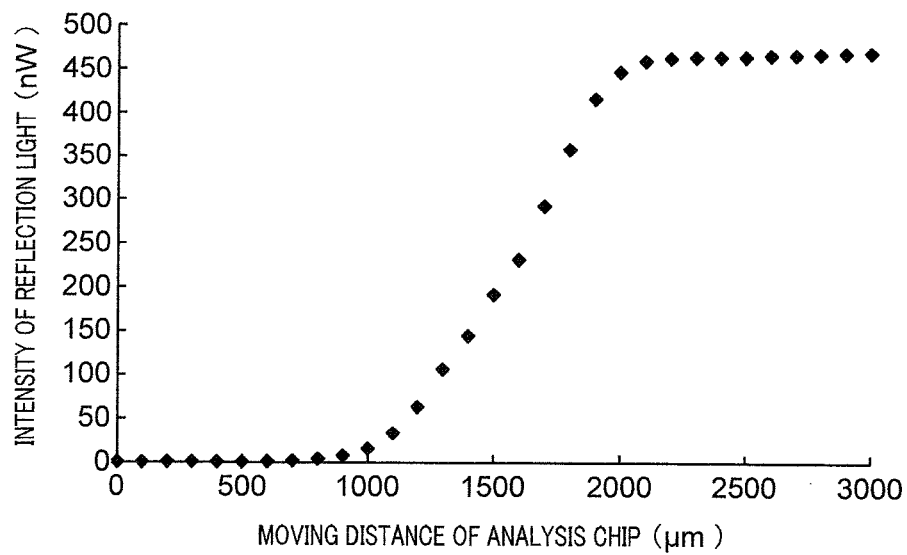
FIGS. 5A and 5B are graphs showing exemplary detection results of reflection light with use of a light receiving sensor.
Figure 5B:
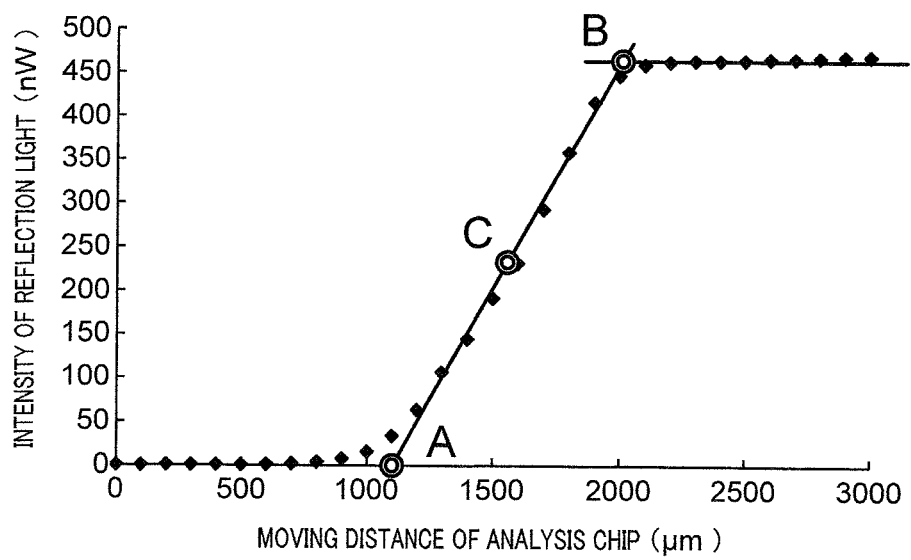

FIGS. 5A and 5B are graphs showing an example of detection results of reflection light β by light receiving sensor 121. In this examples, while moving analysis chip 10 by conveyance stage 152 in one direction (x-axis direction) in units of 100 μm, the intensity of reflection light β was measured with light receiving sensor 121. The beam diameter of excitation light α is about 1 mm to 1.5 mm. FIG. 5A shows only detection results, and FIG. 5B shows three approximation lines together with the detection results.

As illustrated in FIG. 5A, when the moving distance of analysis chip 10 is 0 to approximately 1,000 μm, reflection light β from analysis chip 10 is not incident on light receiving sensor 121. The reason for this is that excitation light α is reflected by channel closure 40 and travels toward the lower side (conveyance stage 152 side) (see FIG. 4A). On the other hand, when the moving distance of analysis chip 10 is approximately 1,000 μm to approximately 2,000 μm, the light amount of reflection light β which is incident on light receiving sensor 121 gradually increases. The reason for this is that part of excitation light α is reflected by incidence surface 21, and is incident on light receiving sensor 121 (see FIG. 4B). When the moving distance of analysis chip 10 is greater than approximately 2,000 μm, the light amount of reflection light β which is incident on light receiving sensor 121 is constant. The reason for this is that the entirety of reflection light β is incident on light receiving sensor 121 (see FIG. 4C). Accordingly, the inclined part (moving distance: approximately 1,000 μm to approximately 2,000 μm) in the graph corresponds to the edge. It is to be noted that the width of the inclined part corresponds to the beam diameter (about 1 mm to 1.5 mm) of excitation light α in the x-axis direction.

In FIG. 5B, the horizontal part of the first half (moving distance: 0 to approximately 1,000 μm), the inclined part (moving distance: approximately 1,000 μm to approximately 2,000 μm), and the horizontal part of the latter half (moving distance: greater than approximately 2,000 μm) are each approximated with a straight line. In the graph, point A is the intersection of the approximation straight line of the horizontal part of the first half and the approximation straight line of the inclined part. Point B is the intersection of the approximation straight line of the inclined part and the approximation straight line of the horizontal part of the latter half. Point C is the middle point between point A and point B. Point A corresponds to a minimum value of the light amount of reflection light β. Point B corresponds to a maximum value of the light amount of reflection light β. Point C corresponds to an intermediate value of the light amount of reflection light β.

In the graph of FIG. 5B, the position of analysis chip 10 can be specified with use of points A to C. Point A and point B indicate points where an end of the beam of excitation light α reaches the edge. Accordingly, the position of the edge can be specified by considering the beam diameter of excitation light α, and as a result, the position of analysis chip 10 can be specified. On the other hand, point C indicates a point where the center of the beam of excitation light α reaches the edge. When point C is utilized, the position of the edge can be specified without considering the beam diameter of excitation light α, and as a result, the position of analysis chip 10 can be specified. Accordingly, from the viewpoint of suppressing the influence of the beam diameter of excitation light α, it is preferable to use the intermediate value of the amount of reflection light β (or transmission light β') of excitation light α to specify the position of analysis chip 10.

Figure 6A:
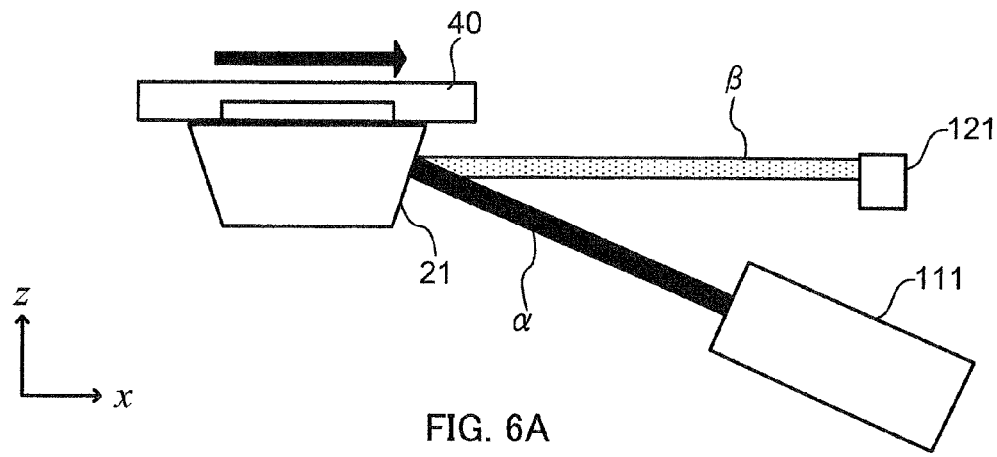
FIGS. 6A to 6C are schematic views for describing a step (S141) of obtaining location information of the analysis chip.
Figure 6B:
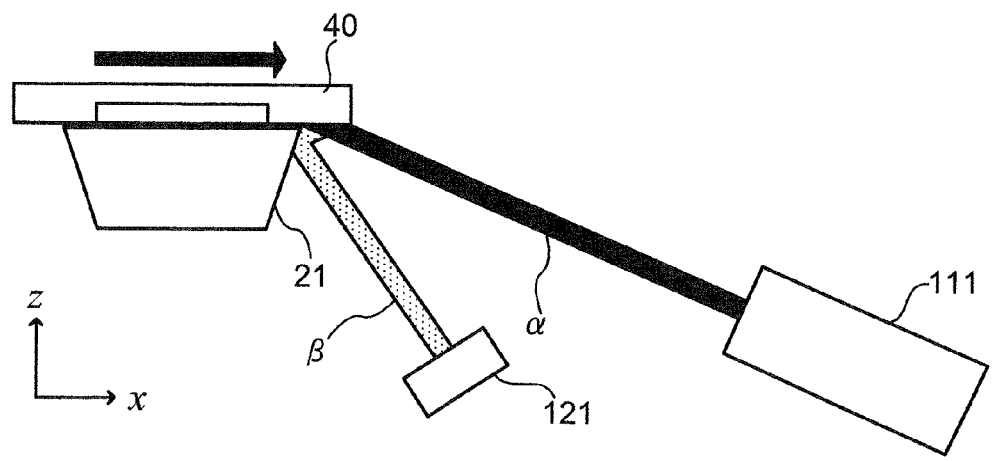

As described, the position of analysis chip 10 can be specified by irradiating analysis chip 10 with excitation light α, and by detecting reflection light β of excitation light α. At this time, as illustrated in FIG. 6A, one surface (in FIG. 6A, incidence surface 21) of analysis chip 10 may be irradiated with excitation light α to specify the position of analysis chip 10. In the example illustrated in FIG. 6A, the light reception surface of light receiving sensor 121 is small, and the position of incidence surface 21 can be specified by determining whether reflection light β is incident on light receiving sensor 121. However, from the viewpoint of specifying the position of analysis chip 10 not only in the horizontal direction (x-axis direction) but also in the height direction (z-axis direction) with high accuracy, it is preferable to specify the position of analysis chip 10 by irradiating two surfaces of analysis chip 10 which are adjacent to each other with excitation light α as illustrated in FIGS. 4A to 4C. In this case, it is preferable to emit excitation light α in a direction which is neither parallel nor perpendicular to the movement direction of chip holder 154 moved by conveyance stage 152. It is to be noted that, also when light receiving sensor 121 is disposed at a position where reflection light β from channel closure 40 is incident but reflection light β from incidence surface 2 is not incident as illustrated in FIG. 6B, an effect similar to that of the exemplary case illustrated in FIGS. 4A to 4C is achieved (the intensity of reflection light β is high when the moving distance is short, and the intensity of reflection light β is low when the moving distance is long).

Figure 6C:
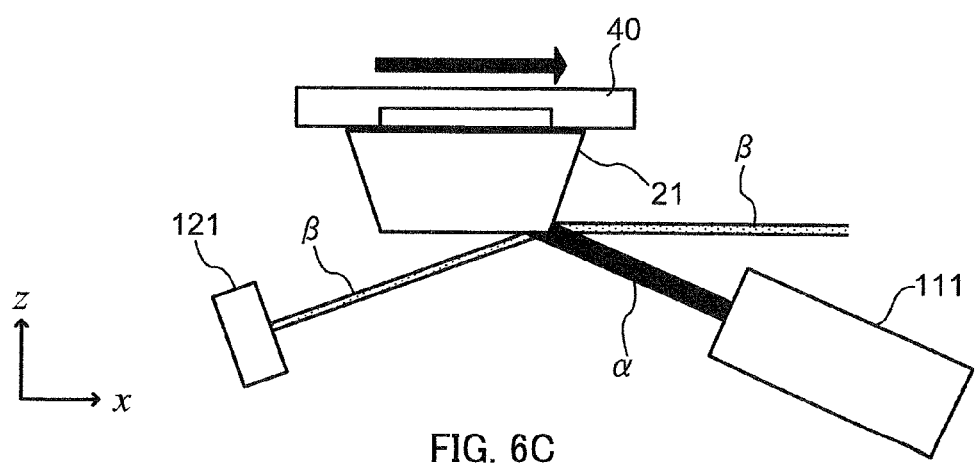

In addition, since the position of incidence surface 21 is an important factor, it is preferable to irradiate incidence surface 21 and a surface adjacent to incidence surface 21 (in the present embodiment, the rear surface of channel closure 40) of analysis chip 10 with excitation light α when two surfaces of analysis chip 10 which are adjacent to each other are irradiated with excitation light α. In this case, it is possible to irradiate incidence surface 21 of prism 20 and the bottom surface of prism 20 with excitation light α as illustrated in FIG. 6C. In the example illustrated in FIG. 6C, however, analysis chip 10 is brought close to light source unit 111 over the measurement position at the time of specifying the position of analysis chip 10 (step S141). Accordingly, when moving analysis chip 10 to the measurement position (step S142), it is necessary to move chip holder 154 in an opposite direction by conveyance stage 152. This operation of conveyance stage 152 in two directions may lead to reduced operation accuracy in comparison with the case where conveyance stage 152 is operated in only one direction. In contrast, in the exemplary case illustrated in FIGS. 4A to 4C and FIGS. 6A and 6B, it is not necessary to move chip holder 154 in opposite directions by conveyance stage 152. Accordingly, from the viewpoint of adjusting the position of analysis chip 10 with high accuracy, it is preferable to move chip holder 154 by conveyance stage 152 only in a direction (x-axis direction) toward the light source of excitation light α (light source unit 111) in the step of obtaining the location information of analysis chip 10 (S141) and the step of moving the analysis chip to the measurement position (S142).

Figure 7:
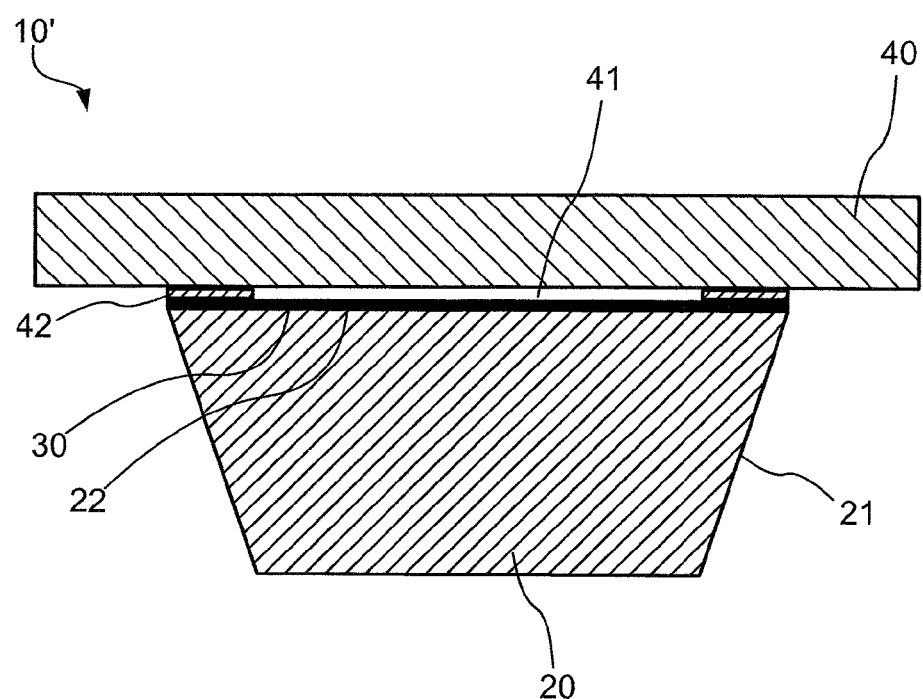
FIG. 7 is a sectional view illustrating another exemplary analysis chip.

It is to be noted that the "two surfaces of analysis chip 10 which are adjacent to each other" include two surfaces substantially adjacent to each other. For example, it is assumed to use analysis chip 10' which has prism 20, metal film 30 disposed on film formation surface 22 of the prism, spacer 42 disposed on metal film 30, and channel closure 40 disposed on spacer 42 as illustrated in FIG. 7. The shape of channel 41 is defined by spacer 42. On the other hand, channel closure 40 is a transparent flat plate. Strictly speaking, in this case, since the side surface of spacer 42 is provided between incidence surface 21 of prism 20 and the bottom surface of channel closure 40, incidence surface 21 and the bottom surface of channel closure 40 are not adjacent to each other. However, in the case where the thickness of spacer 42 is very small (for example, 100 μm) in comparison with the beam diameter (for example, 1 mm to 1.5 mm) of excitation light α, it can be said that incidence surface 21 and the bottom surface of channel closure 40 are substantially adjacent to each other. Accordingly, in this case, reflection light β from incidence surface 21 and the bottom surface of channel closure 40 which are substantially adjacent to each other is detected to detect the edge. Likewise, joining members such as adhesive agent and a doublesided tape, metal film 30, and the like are also negligible.

The thickness of the above-mentioned members (for example, spacer 42) which are negligible at the time of detection of reflection light β is equal to or smaller than $\frac{1}{5}$ of the beam diameter of excitation light α, preferably, equal to or smaller than $\frac{1}{10}$ of the beam diameter of excitation light α. For example, when excitation light α is emitted to a region including spacer 42 whose thickness is equal to or smaller than $\frac{1}{5}$ or equal to or smaller than $\frac{1}{10}$ of the beam diameter of excitation light α, most ($\frac{4}{5}$ or more or $\frac{9}{10}$ or more) of reflection light β from analysis chip 10 is reflection light β from incidence surface 21 or the bottom surface of channel closure 40, and can be utilized for position detection. Accordingly, the position of analysis chip 10 can be specified without being influenced by spacer 42. In this manner, a member (such as spacer 42, a joining member and metal film 30) whose thickness is equal to or smaller than ⅕ of the beam diameter of excitation light α is negligible at the time of detection of reflection light β. That is, incidence surface 21 and the bottom surface of channel closure 40 of analysis chip 10 can be taken as two surfaces which are substantially adjacent to each other.

Figure 8:
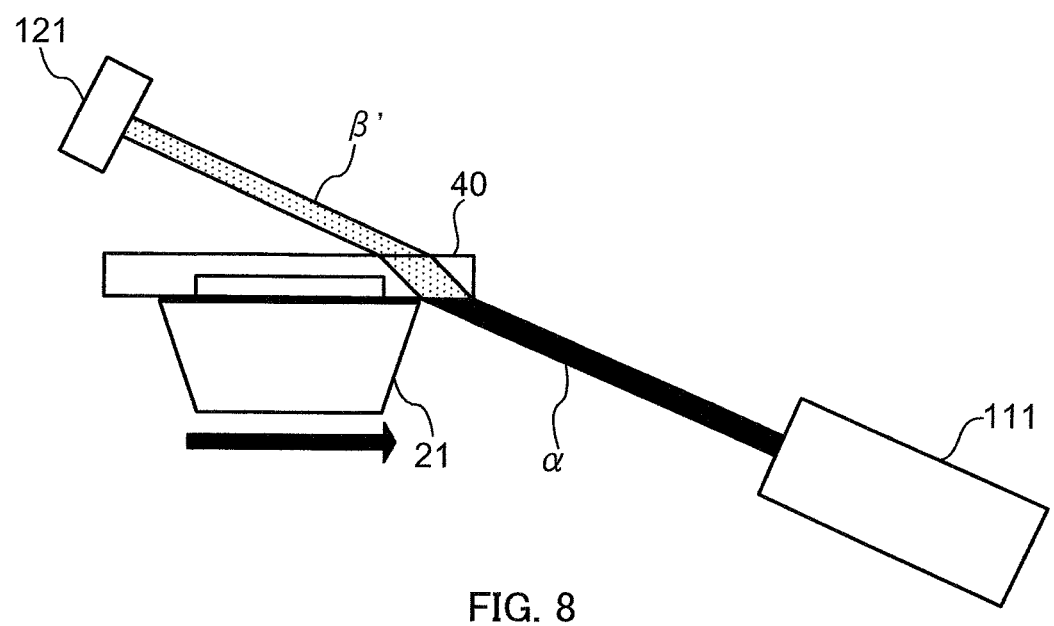
FIG. 8 is a schematic view for describing a step (S141) of obtaining location information of the analysis chip.

In addition, as illustrated in FIG. 8, the position of analysis chip 10 can be specified by detecting transmission light β of excitation light α instead of reflection light β of excitation light α. In the exemplary case illustrated in FIG. 8, transmission light β is generated when excitation light α is incident on channel closure 40. On the other hand, when excitation light α is incident on incidence surface 21, total reflection occurs at film formation surface 22 of prism film 20, and therefore transmission light β is not generated. Accordingly, by detecting transmission light β with light receiving sensor 121, the position of the edge can be specified, and as a result, the position of analysis chip 10 can be specified.

Figure 9A:
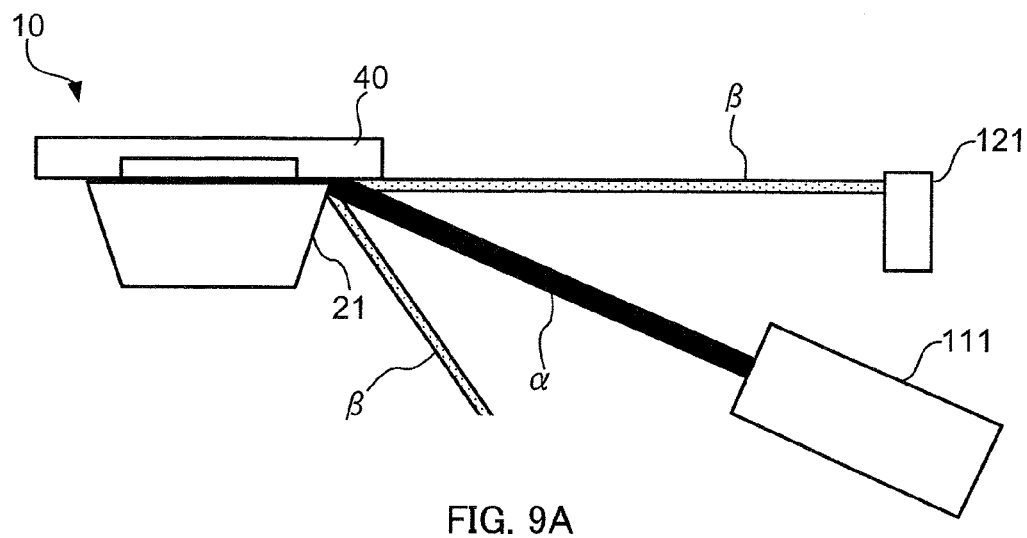
FIGS. 9A and 9B are schematic views for describing a step (S142) of disposing the analysis chip at a measurement position.
Figure 9B:
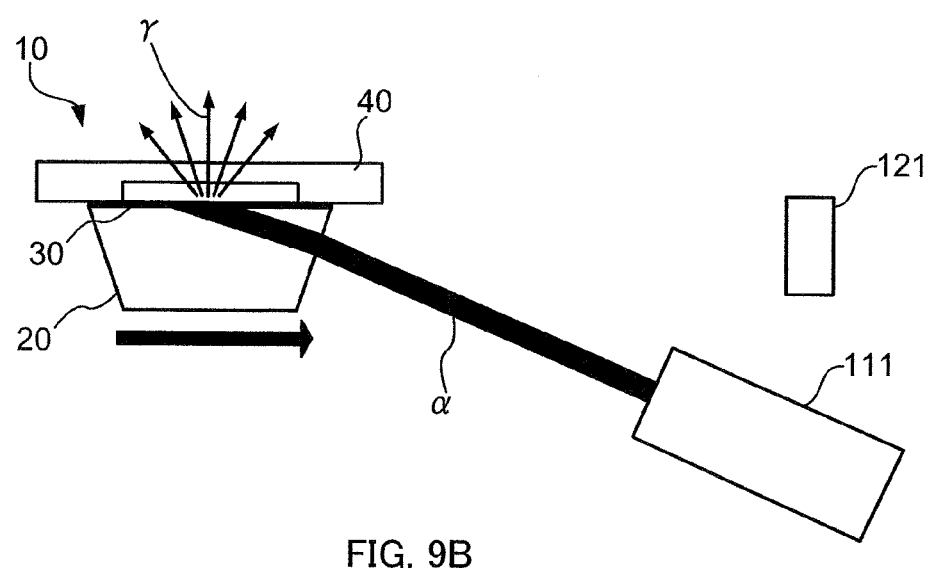

FIGS. 9A and 9B are schematic views for describing a step (step S142) of disposing analysis chip 10 to an appropriate measurement position. First, it is assumed that the position of the edge has been specified as illustrated in FIG. 9A. In this case, since the distance between the position of the edge and the region on the rear surface of metal film 30 to be irradiated with excitation light α (region on the rear side of the reaction site) has been determined, analysis chip 10 can be disposed at an appropriate measurement position by moving chip holder 154 by a predetermined distance by conveyance stage 152 as illustrated in FIG. 9B.

Figure 10A:
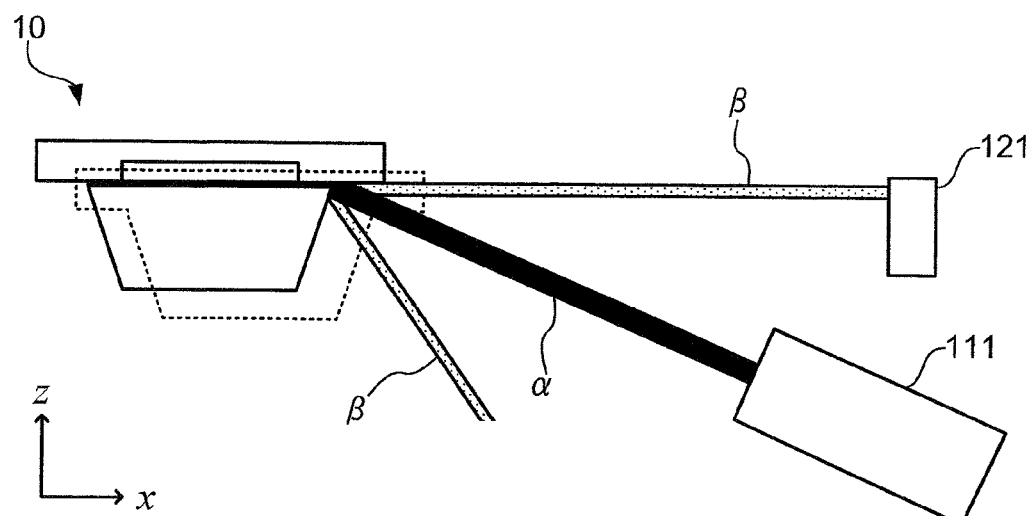
FIGS. 10A and 10B are schematic views for describing a step (S142) of disposing the analysis chip at the measurement position.
Figure 10B:
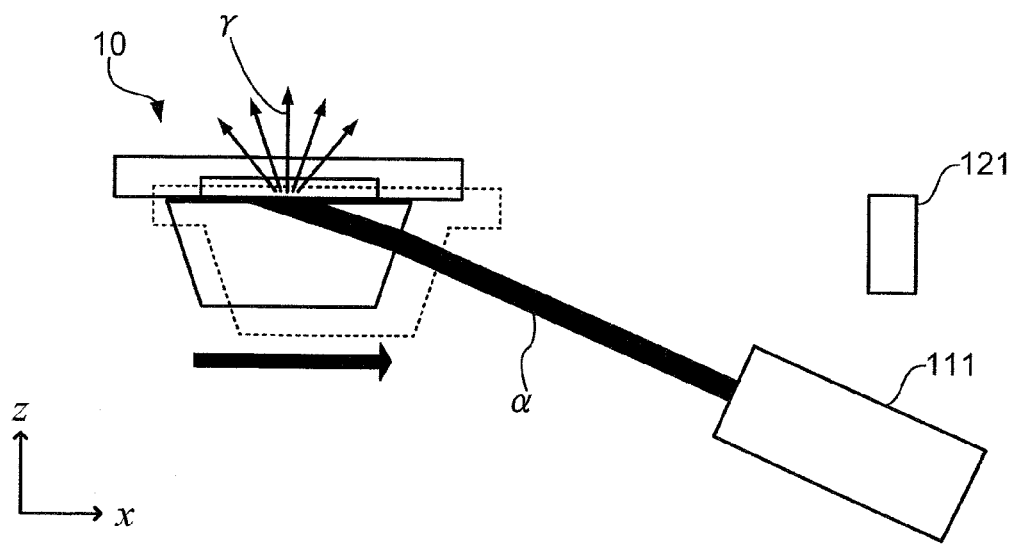

In addition, as illustrated in FIGS. 10A and 10B, even when analysis chip 10 is disposed at a position shifted in a height direction (z-axis direction) (for example, when a foreign matter is sandwiched between analysis chip 10 and chip holder 154), analysis chip 10 can be disposed at an appropriate measurement position. That is, as illustrated in FIG. 10A, it is assumed that the position of the edge has been specified. In this case, the position of analysis chip 10 is shifted in the x-axis direction in comparison with the case where analysis chip 10 is not shifted in the z-axis direction (which is indicated with the broken line in the drawing). However, even in this case, analysis chip 10 can be disposed at an appropriate measurement position by moving chip holder 154 by a predetermined distance by conveyance stage 152 on the basis of the position of the edge as illustrated in FIG. 10B.

The description is returned to the operation procedure of SPFS device 100 (see FIG. 2). Next, control section 160 operates excitation light irradiation unit 110 and fluorescence detection unit 130 to irradiate analysis chip 10 disposed at an appropriate measurement position with excitation light α, and detects plasmon scattering light whose wavelength is identical to excitation light α, thereby detecting the enhanced angle (step S150). To be more specific, control section 160 operates excitation light irradiation unit 110 to scan the incident angle of excitation light α to metal film 30, while operating fluorescence detection unit 130 to detect plasmon scattering light. At this time, control section 160 operates position switching mechanism 132 to dispose optical filter 135 at a position outside the light path of light reception unit 131. Then, control section 160 determines the incident angle of excitation light α at which the light amount of the plasmon scattering light is maximized as the enhanced angle.

Next, control section 160 operates excitation light irradiation unit 110 and fluorescence detection unit 130 to irradiate analysis chip 10 disposed at an appropriate measurement position with excitation light α, and records an output value (optical blank value) of light receiving sensor 137 (step S160). At this time, control section 160 operates angle adjustment mechanism 112 to set the incident angle of excitation light α to the enhanced angle. In addition, control section 160 controls position switching mechanism 132 to dispose optical filter 135 at a position on the light path of light reception unit 131.

Next, control section 160 operates conveyance stage 152 to move analysis chip 10 to a liquid feeding position (step S170).

Next, control section 160 operates liquid feed unit 140 to introduce liquid (labeling solution) including a secondary antibody labeled by a fluorescence material into channel 41 of analysis chip 10 (step S180). In channel 41, through an antigen-antibody reaction (secondary reaction), a substance to be detected which is captured on metal film 30 is labeled by the fluorescence material. Thereafter, the labeling solution in channel 41 is removed, and the interior of the channel is washed with washing solution.

Next, control section 160 operates conveyance stage 152 to move analysis chip 10 to an appropriate measurement position determined at step S140 (step S190).

Next, control section 160 operates excitation light irradiation unit 110 and fluorescence detection unit 130 to irradiate analysis chip 10 disposed at the appropriate measurement position with excitation light α, and detects fluorescence γ emitted from the fluorescence material labelling the substance to be detected captured by the capturing body (step S200). Control section 160 subtracts the optical blank value from the detection value, and calculates the intensity of the fluorescence correlating with the amount of the substance to be detected. The intensity of the fluorescence thus detected is converted to the amount, density, and the like of the substance to be detected as necessary.

Through the above-mentioned procedures, the presence or the amount of a substance to be detected in sample solution can be detected.

Figure 11:
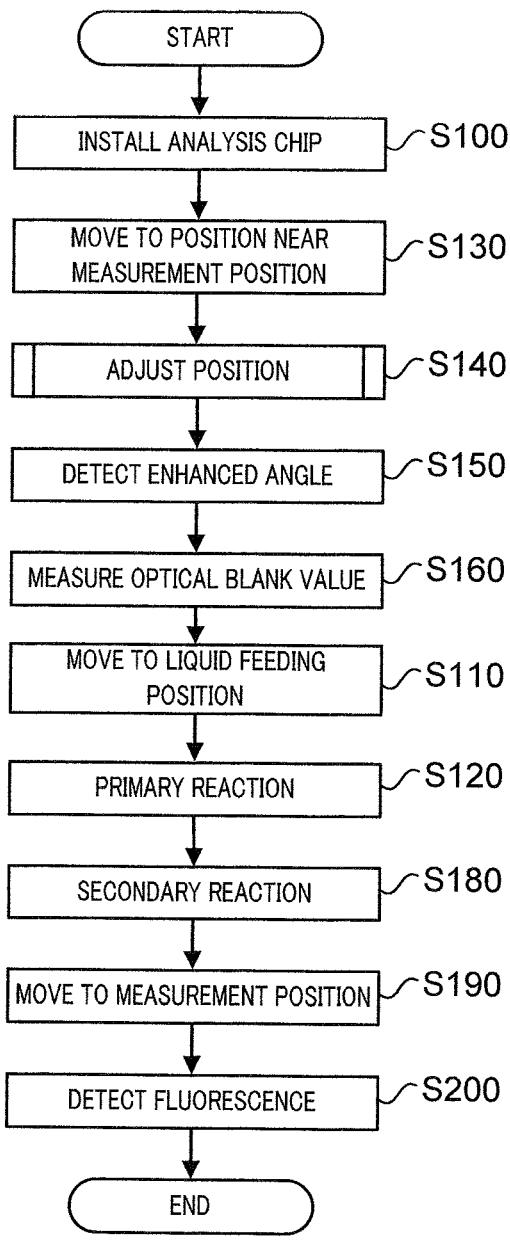
FIG. 11 is a flowchart of another exemplary operation procedure of the SPFS device illustrated in FIG. 1.

It is to be noted that, as illustrated in FIG. 11, the detection of the enhanced angle (step S150) may be performed prior to the primary reaction (step S120). In this case, the determination of the measurement position of analysis chip 10 (step S130 and step S140) is also performed prior to the primary reaction (step S110 and step S120). With this configuration, it is possible to omit the step (step S170) of moving analysis chip 10 to the liquid feeding position which is performed between the primary reaction (step S120) and the secondary reaction (step S180) in the flowchart illustrated in FIG. 2. In addition, the positional accuracy in the step of moving analysis chip 10 to the liquid feeding position (step S110) prior to the primary reaction (step S120) is enhanced, and, in the primary reaction (step S120) and the secondary reaction (step S180), an end of syringe 144 of liquid feed unit 140 can be further surely inserted into analysis chip 10. This moderates the strictness of the positional accuracy of analysis chip 10 which is required in the step of installing analysis chip 10 to chip holder 154 by the user (step S100), thus improving usability.

In addition, in the case where the incident angle of excitation light α is determined in advance, the detection of the enhanced angle (step S150) may be omitted. Also in this case, the determination of the measurement position of analysis chip 10 (step S130 and step S140) is performed prior to the measurement of the optical blank value (step S160). In this manner, it is preferable to perform the determination of the measurement position of analysis chip 10 (step S130 and step S140) before the optical measurement (detection of the enhanced angle, measurement of the optical blank value, or detection of the fluorescence) is performed for the first time.

In addition, in the above description, after the step of causing a reaction between the substance to be detected and the capturing body (the primary reaction, step S120), the step of labelling the substance to be detected with a fluorescence material (the secondary reaction, step S180) is performed (two step method). However, the timing when the substance to be detected is labeled with the fluorescence material is not limited. For example, it is possible to add the labeling solution to the sample solution to preliminarily label the substance to be detected with the fluorescence material before the sample solution is introduced into the channel of analysis chip 10. In addition, the sample solution and the labeling solution may be simultaneously injected into the channel of analysis chip 10. In the former case, by injecting the sample solution into the channel of analysis chip 10, the substance to be detected labeled by the fluorescence material is captured by the capturing body. In the latter case, the substance to be detected is labeled by the fluorescence material, and the substance to be detected is captured by the capturing body. In either case, by introducing the sample solution into the channel of analysis chip 10, both the primary reaction and the secondary reaction can be completed (one step method). When the one step method is employed in this manner, the detection of the enhanced angle (step S150) is performed prior to the antigen-antibody reaction, and the determination of the measurement position of analysis chip 10 (step S130 and step S140) is performed prior to the detection of the enhanced angle.

While the SPFS device is described in the above-mentioned embodiment, the method of positioning the analysis chip according to the embodiment of the present invention is also applicable to analysis devices other than the SPFS device such as an SPR device.

This application is entitled to and claims the benefit of Japanese Patent Application No. 2013-226667 filed on Oct. 31, 2013 the disclosure each of which including the specification, drawings and abstract is incorporated herein by reference in its entirety.

INDUSTRIAL APPLICABILITY

The surface plasmon resonance fluorescence analysis method and the surface plasmon resonance fluorescence analysis device according to the embodiment of the present invention can detect a substance to be detected with high reliability, and therefore is suitable for laboratory test and the like, for example.

REFERENCE SIGNS LIST 10, 10' Analysis chip
20 Prism
21 Incidence surface
22 Film formation surface
23 Emission surface
30 Metal film
40 Channel closure
41 Channel
42 Spacer
100 SPFS device
110 Excitation light irradiation unit
111 Light source unit
112 Angle adjustment mechanism
113 Light source control section
120 Excitation light detection unit
121 Light receiving sensor
122 Sensor control section
130 Fluorescence detection unit
131 Light reception unit
132 Position switching mechanism
133 Sensor control section
134 First lens
135 Optical filter
136 Second lens
137 Light receiving sensor
140 Liquid feed unit
141 Chemical liquid chip
142 Syringe pump
143 Liquid feed pump drive mechanism
144 Syringe
145 Plunger
150 Conveyance unit
152 Conveyance stage
154 Chip holder
160 Control section
α Excitation light
β Excitation light reflection light
β' Excitation light transmission light
γ Fluorescence

The invention claimed is:

1. A surface plasmon resonance fluorescence analysis method in which fluorescence which is emitted from a fluorescence material labelling a substance to be detected when the fluorescence material is excited by localized light based on surface plasmon resonance is detected to detect presence or an amount of the substance to be detected, the surface plasmon resonance fluorescence analysis method comprising:
   installing an analysis chip to a chip holder fixed to a conveyance stage, the analysis chip including a prism having an incidence surface and a film formation surface, a metal film disposed on the film formation surface, and a capturing body fixed on the metal film;
   obtaining location information of the analysis chip by irradiating the analysis chip installed to the chip holder with excitation light, and by detecting reflection light or transmission light of the excitation light;
   moving the analysis chip to a measurement position by moving the chip holder by the conveyance stage based on the location information; and
   irradiating the analysis chip disposed at the measurement position with the excitation light and detecting the fluorescence emitted from the fluorescence material labelling the substance to be detected captured by the capturing body.

2. The surface plasmon resonance fluorescence analysis method according to claim 1, wherein, in the obtaining of the location information of the analysis chip, two surfaces of the analysis chip adjacent to each other are irradiated with the excitation light.

3. The surface plasmon resonance fluorescence analysis method according to claim 2, wherein, in the obtaining of the location information of the analysis chip, the incidence surface and a surface adjacent to the incidence surface of the analysis chip are irradiated with the excitation light.

4. The surface plasmon resonance fluorescence analysis method according to claim 2, wherein, in the obtaining of the location information of the analysis chip, a position of the analysis chip is specified with use of an intermediate value of a light amount of the reflection light or the transmission light of the excitation light.

5. The surface plasmon resonance fluorescence analysis method according to claim 1, wherein, in the obtaining of the location information of the analysis chip, the excitation light is emitted in a direction which is not parallel to or perpendicular to a direction in which the chip holder is moved by the conveyance stage.

6. The surface plasmon resonance fluorescence analysis method according to claim 1, wherein, in the obtaining of the location information of the analysis chip, reflection light from the incidence surface is detected.

7. The surface plasmon resonance fluorescence analysis method according to claim 1, wherein, in the obtaining of the location information of the analysis chip and in the moving of the analysis chip to the measurement position, the chip holder is moved by the conveyance stage only in a direction toward a light source of the excitation light.

8. A surface plasmon resonance fluorescence analysis device in which fluorescence which is emitted from a fluorescence material labelling a substance to be detected when the fluorescence material is excited by localized light based on surface plasmon resonance is detected to detect presence or an amount of the substance to be detected, the surface plasmon resonance fluorescence analysis device comprising:

a chip holder configured to detachably hold an analysis chip, the analysis chip including a prism including an incidence surface and a film formation surface, a metal film disposed on the film formation surface, and a capturing body fixed on the metal film;

a conveyance stage configured to move the chip holder;

a light source configured to irradiate the analysis chip held by the chip holder with excitation light;

an excitation light detection sensor configured to detect the excitation light reflected by the analysis chip or the excitation light transmitted through the analysis chip;

a position adjuster configured to, based on a detection result of the excitation light detection sensor, specify a position of the analysis chip held by the chip holder, and move the chip holder by the conveyance stage to move the analysis chip to a measurement position; and a fluorescence detection sensor configured to detect the fluorescence emitted from the fluorescence material labelling the substance to be detected captured by the capturing body.

\* \* \* \* \*